(12) United States Patent
Adjei et al.

(10) Patent No.: US 6,585,957 B1
(45) Date of Patent: *Jul. 1, 2003

(54) MEDICINAL AEROSOL FORMULATION

(75) Inventors: Akwete L. Adjei, Bridgewater, NJ (US); Yaping Zhu, Highland Park, NJ (US); John Z. Sun, Edison, NJ (US); Simon Stefanos, Morris Plains, NJ (US)

(73) Assignee: Aeropharm Technology Incorporated, Edison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/702,195

(22) Filed: Oct. 30, 2000

Related U.S. Application Data

(60) Provisional application No. 60/177,987, filed on Jan. 25, 2000.

(51) Int. Cl.[7] .............................. A61K 9/12; A61K 9/14; A61K 38/28; A61M 15/00; A61M 11/08
(52) U.S. Cl. ........................... 424/45; 424/43; 424/44; 514/4; 514/866; 128/200.14; 128/200.21; 128/200.23
(58) Field of Search .............................. 424/45, 44, 43; 514/4, 866; 128/200.14, 200.21, 200.23

(56) References Cited

U.S. PATENT DOCUMENTS

| 5,011,678 A | | 4/1991 | Wang et al. | |
|---|---|---|---|---|
| 5,594,015 A | | 1/1997 | Kurtz et al. | |
| 5,635,159 A | | 6/1997 | Fu Lu et al. | |
| 5,744,123 A | * | 4/1998 | Akehurst et al. | 424/45 |
| 6,136,294 A | * | 10/2000 | Adjei et al. | 424/45 |
| 6,193,954 B1 | | 2/2001 | Adjei et al. | |

FOREIGN PATENT DOCUMENTS

| WO | WO 90 009781 A | 9/1990 |
|---|---|---|
| WO | WO 96 19198 A | 6/1996 |

OTHER PUBLICATIONS

Patton et al., Advanced Drug Delivery Reviews, 8(1992) 179–196.

* cited by examiner

Primary Examiner—Frederick Krass
Assistant Examiner—Clinton Ostrup
(74) Attorney, Agent, or Firm—Frommer Lawrence & Haug LLP

(57) ABSTRACT

A medicinal formulation is disclosed. The formulation comprises (a) a protein or peptide medicament; (b) a fluid carrier for containing said medicament; and a stabilizer selected from an amino acid, a derivative thereof or a mixture of the foregoing.

18 Claims, No Drawings

MEDICINAL AEROSOL FORMULATION

This application claims priority from U.S. provisional application Ser. No. 60/177,987 filed Jan. 25, 2000, which is incorporated herein by reference.

BACKGROUND OF THE INVENTION

1. Field of the Invention

This invention relates to a medicinal aerosol formulation, and more particularly, to a medicinal aerosol formulation comprising a protective colloid stabilizer.

2. Description of the Related Art

Delivery of drugs to the lung by way of inhalation is an important means of treating a variety of conditions, including such common local conditions as cystic fibrosis, pneumonia, bronchial asthma and chronic obstructive pulmonary disease and some systemic conditions including pain management, immune deficiency, hormonal therapy, erythropoiesis, diabetes, etc. Steroids, (β2 agonists, anticholinergic agents, proteins and polypeptides are among the drugs that are administered to the lung for such purposes. Such drugs are commonly administered to the lung in the form of an aerosol of particles of respirable size (less than about 10 μm in diameter). In order to assure proper particle size in the aerosol, particles can be prepared in respirable size and then incorporated into a colloidal dispersion containing either a propellant, as a pressurized metered dose inhaler (MDI), or air such as is the case with a dry powder inhaler (DPI). Alternatively, formulations can be prepared in solution or emulsion form in order to avoid the concern for proper particle size in the formulation. Solution formulations must nevertheless be dispensed in a manner that produces particles or droplets of respirable size.

For MDI preparations, once prepared, the aerosol formulation is filled into an aerosol canister equipped with a metered dose valve. In the hands of the patient the formulation is dispensed via an actuator adapted to direct the dose from the valve to the patient.

It is important that an aerosol formulation be stable such that the delivered dose discharged from the metered dose valve is reproducible. Rapid creaming, settling, or flocculation after agitation are common sources of dose irreproducibility in suspension formulations. This is especially true where a binary aerosol formulation containing only medicament and propellant, e.g. 1,1,1,2-tetrafluoroethane, is employed or where such formulation contains small amounts of surfactant as well. Sticking of the valve also can cause dose irreproducibility. In order to overcome these problems, MDI aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents, such as ethanol, have been used to overcome this problem, as described in U.S. Pat. No. 5,225,183. An alternative approach that avoids cosolvents involves materials that are soluble or homogeneously dispersible in hydrofluorocarbon propellants and are said to be effective surfactants or dispersing aids in an aerosol formulation. Among such materials are certain fluorinated surfactants and certain polyethyoxysurfactants.

Medicaments which are relatively small molecules are much more predictable in terms of their aerosol formulation characteristics than macromolecules. The macromolecules, such as peptides or proteins, which range in molecular size from about 1K Dalton to about 150 K Daltons in molecular size are very unpredictable and present unique problems in forming aerosol formulations thereof which are stable and provide reproducible dosage.

Most peptide and protein drugs, such as hormones, e.g. insulin, amylin, etc., enzymes, antinfectives, are quite variable in their amino acid composition and three-dimensional structure. Consequently their surface activity is highly variable, and importantly, no model is yet available that explains differences in protein surface activity based on their most basic and structural properties, such as molecular weight, adsorptivity, solubility, partition coefficient and isoelectric pH. Hemoglobin, for example, has far higher affinity for solid surfaces than does albumin, yet the molecular weights of these two proteins are very similar. Fundamentally, the diversity in surface activity of peptides and proteins originates in the linear sequence of amino acids that uniquely characterizes each type of protein. The amino acid side chains often vary dramatically in that some carry no charge at any pH, yet exhibit considerable polar character (serene, threonine). Other amino acids are ionizable and vary from fairly acidic (aspartic and glutamic acid are fully negatively charged at the physiological pH of 7.4) to basic functionalities, such as the imidazole group in histidine (which carries a partial positive charge at pH 7.4), and the still more basic amino groups in lysine and arginine that carry full positive charges at pH 7.4. Another group of amino acids, somewhat hydrocarbon-like in character, appear to demonstrate generally a much lower solubility profile in water (tryptophan, phenylalanine, isoluecine, etc.) than many of the other amino acids found in biological systems. It is noteworthy that the hydrophobicity of these water-hating amino acids varies greatly with their specific structure in the protein. For example, the single methyl group side chain in alanine contributes only 0.5 kcal/mole to the free energy of transfer from water to an organic phase, whereas the double-ringed indole group in tryptophan contributes 3.4 kcal. The variety of amino acid side chains, together with the many different types of chemical interactions that result in solution and at surfaces, should be expected to have a considerable impact on aerosol formulation stability as well as transport of these peptide and protein biotherapeutic agents across biologic membranes.

The diverse character of the amino acid side chains, together with the complexity of various combinations of amino acids present in each particular protein, means that physicochemical properties of the proteins, their intermolecular as well as intramolecular Fax reactivity, and also their ability to interact with surfaces should be highly variable. Due to their large size, and correspondingly due to the large numbers of charged amino acid side chains, proteins have many charges distributed over their exterior surface. This could lead to very large variances in aerosol formulation stability and lung uptake of these compounds. Peptide and protein drugs also generally have multiple ionization sites and therefore they often demonstrate pH-dependent solubility profiles. Importantly, the hydrophilic nature of these compounds provides excellent conditions for high aqueous solubility. Consequently, most peptide and protein drugs present extremely low lipid solubility characteristics, the latter possibly being one reason why dispersions of these drugs in hydrofluorocarbon propellants would be physically and chemically stable across a wide range of storage conditions. An aerosol medicament formulation comprising peptide and protein drugs in carrier or formulation media within which they are virtually insoluble is needed to reduce hydrolytic and chemical deactivation usually typical of aqueous solutions.

The combination of a large surface area, thin absorptive carrier, and extensive vasculature constitutes a favorable absorptive environment for proteins and peptides when delivered by the pulmonary route. Studies show that intratracheal (i.t.) administration of peptides is rapid and quantifiable; however the resultant distribution is often localized in central airways. Administration by aerosol, for example, depending on particle size distribution, may be used to give more uniform distribution with greater alveolar penetration. Drug absorption from the airways is dependent upon the site of deposition, the method of drug delivery, the type of solute presentation and composition of the formulation. Therefore, formulation and device characteristics will have a dramatic impact upon the rate and extent of peptide absorption from the lung. Studies show that absorption rates following aerosol delivery of small molecular weight compounds can be roughly twice that of i.t. delivery. What is desired is to present peptides and proteins as hydrophobic dispersions via a multi dose inhalation device ("pMDI") in order to have greater penetration of the drug particles to the peripheral lung where absorption should be significantly greater than it is for centrally deposited drug as is the case with aqueous instillations.

The realty that insulin can be absorbed from the lung into the bloodstream has been demonstrated by a number of scientists. A 1990 review article [*Lung, supplement* pp. 677–684] demonstrated from multiple studies that aerosolized insulin delivered into the lung yielded a half-life of 15–25 minutes but results were quite variable. Comprehensive studies also have demonstrated that aerosolized insulin given peripherally into the lung of rabbits produced bioavailability of over 50.7 percent in contrast to 5.6 percent bioavailability seen for liquid insulin dripped into the central airways. These studies therefore support the contention that aerosolized insulin must be delivered peripherally into the lung for maximum efficiency and that inadvertent central disposition of inhaled aerosolized insulin will produce an effect ten times lower than that desired. Such variations in dosing of ten-fold are clearly unacceptable if aerosolized insulin should become an effective means of treating diabetes. Thus, there is need for effective, high precision aerosol devices to achieve the tolerances required for aerosolizing insulin to human subjects. This concept for using aerosolized insulin in diabetes management would also apply to amylin and glucagon, partner hormones to insulin in the regulation of plasma glucose concentrations, which until now, must be administered by subcutaneous injection (s.c.).

Dry powder presentations of peptide and protein drugs possess unique opportunities in formulations, which do not occur in liquid presentations such as pMDIs and nebulized solutions. Dry powder aerosols of peptide and protein drugs, because of improved solid state stability, are attractive from the formulation standpoint since many of the undesirable solution and liquid state interactive effects are circumvented. In this regard, reference is made to Rubsamen et al., U.S. Pat. No. 5,672,581 and Patton et al. in U.S. Pat. No. 5,775,320.

Both the Rubsamen and Patton approaches are therapeutically feasible although their complexity and presumed inherent costs limit their applicability to the management of a chronic disease like diabetes mellitus. Thus, it is a problem to use an expensive, complicated device such as the portable, electronically based portable nebulizer to routinely deliver hypoglycemics to patients that need them. It is further a problem to use large, bulky, difficult to clean a dry powder aerosol device like the Patton device to deliver the hypoglycemics to the body via lung. Thus, the primary objective in formulating a peptide or protein drug as a dry powder inhalation aerosol (DPI) is to enable the drug, and in some cases, added excipients, to form an aerocolloid which is chemically and physical stable and can remain in suspension until the drug particle reaches the alveolar or other absorption sites. Once at the absorption site, the drug particles should be efficiently trapped at the deposition site, dissolve rapidly in the epithelial lining fluids, and be absorbed quickly across the biomembrane thereby limiting possible deactivation by metabolizing enzymes in the airways.

Spray drying is a process used to prepare medicament particles for drug formulations. Spray drying constitutes a single step process which transforms a solution or suspension into fine powder. Generally, spray drying produces spherical particles, which are often hollow thus resulting in a powder with low bulk density compared to the initial material. Powder characteristics of spray dried materials (i.e., particle size distribution, bulk density, porosity, moisture content, dispersibility, etc.) are generally good in many regards, but particles manufactured by this process demonstrate poor flow characteristics. Furthermore, a requirement for heat during particle formation by this process makes spray drying less desirable for heat sensitive compounds such as peptide and protein drugs. Thus, it is a problem that most dry powder aerosols demonstrate adhesion and poor flowability through device hardware to the extent that accuracy of dose delivery becomes a problem to the patient.

Another problem associated with peptide and protein formulations as dry powder aerosols is that of packaging the material as agglomerates in a device such that during aerolization, the agglomerates are broken up, and the individual particles released prior to entry into the airways. Preparation of robust agglomerates of micron or sub-micron sized particles is a reasonably straightforward task which can be achieved by conventional granulation, with or without polymeric binders. However, the requirement that upon entering the airways, the agglomerates should break up into primary particles, probably rules out a simple, conventional approach to granulation since the interparticle forces could be too large to allow easy, efficient and prompt deagglomeration. The total adhesive force between two unlike particles or total cohesive force between two like particles can be considered as being constituted from a sum of one or more attractive forces. Many of these forces are known to be responsible for formation of adhesive units between dry powder and excipient particles in formulations. Therefore the aim of any manipulation of inter-particle forces will be to produce agglomerates of between say, 50 and 200 $\mu$m diameter, which are robust enough to withstand flow, storage and packing in the delivery device, but which can be de-agglomerated rapidly and completely by the shear stresses in the inspired air stream. This problem which is quite common in peptide and protein aerosol formulations may be avoided completely in liquid formulations within which the drug is insoluble, is presented as a colloidal dispersion, and is sterically protected against self-association. Hence it is a desire to formulate peptide and protein drugs as loose, flocculated colloids in non-aqueous media, like hydrofluorocarbons, which rapidly and easily break up into discrete particles upon aerolization to the airways. Additionally, it is desired to present peptide and protein drugs in formulation systems within which the drug particles are perpetually in random motion, thus eliminating aggregate formation of the individual drug particles.

Other non-injectable diabetes therapies have been proposed, some demonstrating that a biotherapeutic response could be produced following nasal administration of insulin when formulated with detergents and other membrane penetrants, as indicated in Moses et al., *Diabetes*, Vol. 32, November 1983, and Salzman et al., *New England Journal of Medicine*, Vol. 312, No. 17. Significant intersubject variability and irritation of nasal membranes to varying degrees is observed. Since diabetes is a chronic disease which must be continuously treated by the administration of insulin, and since mucosal irritation tends to increase with repeated exposures to membrane penetration enhancers, efforts at developing a non-invasive nasally administered insulin have not been commercialized. Accordingly, a safe, reproducible, effective, non-invasive delivery means for peptide and protein drugs via lung as pMDIs is desired and needed.

SUMMARY OF THE INVENTION

It has surprisingly been found that novel and stable medicinal aerosol formulations of macromolecular medicaments can be obtained without the use of either cosolvents, such as ethanol, or surfactants, such as sorbitan trioleate which are added to a binary aerosol formulation of small molecule medicaments. Stable medicinal aerosol formulations are obtained by the use of a protective colloid stabilizer.

DETAILED DESCRIPTION OF THE INVENTION

This application makes references to U.S. application Ser. No. 09/158,369 filed Sep. 22, 1998, now U.S. Pat. No. 6,136,294, which issued on Oct. 24, 2000, which is incorporated hereinto by reference in its entirety.

This invention involves a stable suspension aerosol formulation suitable for pressurized delivery which comprises (1) a particulate macromolecular medicament or drug, (2) a suitable propellant, and (3) a suitable stabilizer.

A suitable macromolecular medicament or drug is one which is suitable for administration by inhalation, the inhalation being used for oral and nasal inhalation therapy. A stable, colloidal dispersion of a medicament in a fluid, e.g. air, hydrocarbon gases, chlorofluorocarbon (CFC) propellants or non-CFC propellants, such as tetrafluoroethane (HFA-134a) and heptafluoropropane (HFA-227) is described.

A stabilizer of a polyionic species, such as an amino acid and a small molecule peptide, as inactive formulation components which trigger loss of adhesive bond strength between the medicament particles is employed. An electret or sterially stabilized aerocolloid particles of the selected medicaments is thus formed. Electrets are the electrostatic equivalent of permanent magnets but can be susceptible to breakdown in the presence of moisture, such as that present in air or at ambient humidity conditions of the respiratory tract. Accordingly the present invention applies to dry powder aerosols, portable nebulizer systems, as well pressurized metered dose inhaler formulations.

The resultant aerocolloid is chemically and physically stable and can remain in suspension until the selected medicament or drug particles reach the alveolar or other absorption sites in the airways of a patient, e.g. human, animal, being treated. Once at the absorption site, the drug particles should be efficiently trapped at the deposition site as a result of moisture in the ambient, dissolve rapidly in the epithelial lining fluids, and be absorbed quickly across the biomembranes of the patient, thereby limiting possible deactivation by metabolizing enzymes in the airways.

A suitable medicament to which the subject invention is directed is one that forms a stable hydrophobic dispersion suitable for delivery to a patient, e.g., human or animal. Typically, the medicament includes a peptide, polypeptide, or protein biotherapeutic ranging from 0.5 K Dalton to 150 K Dalton in molecular size. In particular, the peptide, polypeptide, or protein biotherapeutic medicament includes diabetic aids; insulins and insulin analogs; amylin; glucagon; surfactants; immunomodulating peptides such as cytokines, chemokines, lymphokines interleukins such as taxol, interleukin-1, interleukin-2, and interferons; erythropoetins; thrombolytics and heparins; anti-proteases, antitrypsins and amiloride; rhDNase; antibiotics and other anti-infectives; hormones and growth factors such as parathyroid hormones, LH-RH and GnRH analogs; nucleic acids; DDAVP; calcitonins; cyclosporine; ribavirin; enzymes; heparins; hematopoietic factors; cyclosporins; vaccines; immunoglobulins; vasoactive peptides; antisense agents; genes, oligonucleotides, and nucleotide analogs.

The term diabetic aid includes natural, synthetic, semi-synthetic and recombinant medicaments such as activin, glucagon, insulin, somatostatin, proinsulin, amylin; and the like.

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain or amino acid sequences which act as insulin in decreasing blood glucose levels. In general, the "insulin analogs" of the present invention include "insulin lispro analogs," as disclosed in U.S. Pat. No. 5,547,929, incorporated hereinto by reference in its entirety, insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin such as insulin lispro i.e., compounds which are administered to reduce blood glucose levels.

The term "amylin" includes natural human amylin, bovine, porcine, rat, rabbit amylin, as well as synthetic, semi-synthetic or recombinant amylin or amylin analogs including pramlintide and other amylin agonists as disclosed in U.S. Pat. No. 5,686,411, and U.S. Pat. No. 5,854,215, both of which are incorporated hereinto by reference in their entirety.

The term "immunomodulating proteins" include cytokines, chemokines, lymphokines complement components, immune system accessory and adhesion molecules and their receptors of human or non-human animal specificity. Useful examples include GM-CSF, IL-2, IL-12, OX40, OX40L (gp34), lymphotactin, CD40, CD40L. Useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, ICAM-1, 2 or 3 and cytokine a receptors. OX40 and OX40-ligand (gp34) are further useful examples of immunomodulatory proteins. Immunomodulatory proteins can for various purposes be of human or non-human animal specificity and can be represented for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular origin and antigenicity, alpha-interferon (leukocytes), beta-interferon (fibroblasts) and gamma-interferon (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. See also Viscomi, 1996 Biotherapy 10:59–86. The terms "alpha.-interferon", "alpha interferon", "interferon alpha", "human leukocyte interferon" and IFN are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acid sequences. Purified natural human alpha inteferons and mixtures thereof which may be used in the practice of the invention include but are not limited to Sumiferon RTM interferon alpha-n1 available from Sumitomo, Japan; Welfferong interferon alpha-nl (Ins) available from Glaxo-Welicome Ltd., London, Great Britain; and Alferon RTM interferon alpha-n3 available from the Purdue Frederick C., Conn.

The term "erythropoietin" applies to synthetic, semi-synthetic, recombinant, natural, human, monkey, or other animal or microbiological isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eucaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) cells may be further characterized by freedom from association with human proteins or other contaminants which may be associated with erythropoietin in its natural mammalian cellular environment or in extracellular fluids such as plasma or urine. The products of typical yeast (e.g., Saccaromyces cerevisiae) or procaryote (e.g., E. coli) host cells are free of association with any mammalian proteins. Depending upon the host employed, polypeptides of the invention may be glycosylated with mammalian or other eucaryotic carbohydrates or may be nonglycosylated. Polypeptides of the invention may also include an initial methionine amino acid residue (at position -1). Novel glycoprotein products of the invention include those having a primary structural conformation sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

The terms "heparins" and "thrombolytics" include anti-clotting factors such as heparin, low molecular weight heparin, tissue plasminogen activator (TPA), urokinase (Abbokinase) and other factors used to control clots.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). The list also includes antibodies which recognize self-antigens such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, thyroid releasing hormone (TRH), gonadotropin-releasing hormone (GnRH), leuteininzing hormone, leuteininzing hormone-releasing hormone (LHRH, including the superagonists and antagonists such as leuprolide, deltirelix, gosorelin, nafarelin, danazol, etc.) sourced from natural, human, porcine, bovine, ovine, synthetic, semi-synthetic, or recombinant sources. These also include somatostatin analogs such as octreotide (Sandostatin). Other agents in this category of biotherapeutics include medicaments for uterine contraction (e.g., oxytocin), diuresis (e.g., vasopressin), neutropenia (e.g., GCSF), respiratory disorders (e.g., superoxide dismutase), RDS (e.g., surfactants, optionally including apoproteins), and the like.

The term "enzymes" include recombinant deoxyribonuclease such as DNAse (Genentech) from Corporation, proteases (e.g., serine proteases such as trypsin and thrombin), polymerases (e.g., RNA polymerases, DNA polymerases), reverse transcriptases and kinases, enzymes implicated in arthritis, osteoporosis, inflammatory diseases, diabetes, allergies, organ transplant rejection, oncogene activation. (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized and selected in accordance with the invention include, but are not limited to, a gonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

The term "analog" refers to a molecule, which shares a common functional activity with the molecule to which it is deemed to be an analog and typically shares common structural features as well.

The term "recombinant" refers to any type of cloned biotherapeutic expressed in procaryotic cells or genetically engineered molecule, or combinatorial library of molecules which may be further processed into another state to form a second combinatorial library, especially molecules that contain protecting groups which enhance the physicochemical, pharmacological, and clinical safety of the biotherapeutic agent.

The term "vaccines" refers to therapeutic compositions for stimulating humoral and cellular immune responses, either isolated, or through an antigen presenting cell, such as an activated dendritic cell, that is able to activate T-cells to produce a multivalent cellular immune response against a selected antigen. The potent antigen presenting cell is stimulated by exposing the cell in vitro to a polypeptide complex. The polypeptide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still other preferred embodiments, the polypeptide antigen may be any one of the oncogene product peptide antigens. The polypeptide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigens, are also within the contemplation of the invention.

The term "immunoglobulins" encompasses polypeptide oligonucleotides involved in host defense mechanisms such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

For purposes of the formulations of this invention, which are intended for inhalation into the lungs, the medicament or drug is preferably micronized whereby a ski therapeutically effective amount or fraction (e.g., ninety percent or more) of the drug is particulate. Typically, the particles have a diameter of less than about 10 microns, and preferably less than about 5 microns, in order that the particles can be inhaled into the respiratory tract and/or lungs.

The selected medicament or drug is present in the inventive formulations in a therapeutically effective amount, that is, an amount such that the drug can be administered as a dispersion, aerosol, via oral or nasal inhalation, and cause its desired therapeutic effect, typically preferred with one dose, or through several doses. The drug is typically administered as an aerosol from a conventional valve, e.g., a metered dose valve, through an aerosol adapter also known as an actuator.

The term "amount" as used herein refers to a quantity or to a concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.001 parts by weight to about 5 parts by weight based on 100 parts by weight of the fluid or propellant selected.

A suitable fluid includes air, a hydrocarbon such as n-butane, propane, isopentane, etc. or a propellant. A suitable propellant is any fluorocarbon, e.g. a 1–6 hydrogen containing flurocarbon (such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as propellants 11, 12 and 114 or amixture thereof. Non-CFC propellants such as 1,1,1,2-tetrafluoroethane (Propellant 134a), 1,1,1,2,3,3,3-heptafluoropropane (Propellant 227) or a mixture thereof are preferred. The fluid or propellant is preferably present in an amount sufficient to propel a plurality of the selected doses of drug from an aerosol canister when such is employed.

A suitable stabilizer is selected. A suitable stabilizer includes (1) an amino acid selected from (a) a monoamino carboxylic acid of the formula, $H_2N-R-COOH$ (I), (b) a monoamino dicarboxylic acid of the formula, H₂N—R(COOH)₂ (II) and (c) a diamino monocarboxylic acid of the formula (H₂N)₂—R COOH (III), where R is a straight or branched alkyl radical of from 1 to 22 carbon atoms, which can be mono or poly-substituted with moieties such as sulfide (—S—), oxide (—O—), hydroxyl (—OH), amide (—NH), sulfate (—SO4); aryl of the formula

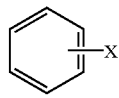

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, di-peptides, e.g. salts and esters of oxidized and unoxidized L-cysteinylglycine, gamma-L-glutamyl-L-cysteine, N-acetyl-L-cysteine-glycine, either conjugated, unconjugated or polymeric forms of L-Gly-L-Glu and L-Val-L-Thr, L-aspartyl-L-phenylalanine, muramyl dipeptides, nutrients such as L-tyrosyl-L-tyrosine, L-alanyl-L-tyrosine, L-arginyl-L-tyrosine, L-tyrosyl-L-arginine, N-Cbz-L-Leu-L-Leu-OCH and its salts or esters, glycyl-glycine, N-acetyl-L-aspartate-L-glutamate (NAAG), etc.; and tripeptides, e.g. oxidized and unoxidized gamma-L-glutamyl-L-cysteinylglycine; muramyl tripeptides, etc. (c) esters of the carboxylic acid group obtained from aliphatic straight or branched chain alcohols of from 1 to 6 carbon atoms, e.g. L-aspartyl-L-phenylalanine methylester (Aspartame®), (3) an ether of any of the foregoing; (4) a hydrate or semi-hydrate of any of the foregoing and (5) a mixture of the amino acid and the derivative of the amino acid.

Suitable amino acids of the formula I include glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula 11 include, aspartic acid, and glutamic acid, compounds of the formula (III) include arginine, glutamine, lysine, hydroxylysine, omithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

For optimal functional and therapeutic performance of the aerosol formulation, either as a dry powder or as an aerosol suspension, the stabilizer is present either as a coarse carrier (e.g., 20–90 μm) or as a finely micronized powder, ≦10 μm in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.001 parts per million to about 200,000 parts per million, more preferably about 1 part per million to about 10,000 parts per million, most preferably from about 10 parts per million to about 5,000 parts per million of the total formulation.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

Generally the formulations of the invention can be prepared by combining (i) the drug in an amount sufficient to provide a plurality of therapeutically effective doses; (ii) the stabilizer in an amount effective to stabilize each of the formulations; (iii) the fluid or propellant in an amount sufficient to propel a plurality of doses, e.g. from an aerosol canister; and (iv) any further optional components e.g. ethanol as a cosolvent; and dispersing the components. The components can be dispersed using a conventional mixer or homogenizer, by shaking, or by ultrasonic energy. The components can also be dispersed using a bead mill or a microfluidizer. Bulk formulations can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

Conventional nebulizer systems can be employed with the formulations of this invention, as well as by powder aerosols.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

We claim:

1. A medicinal aerosol formulation, which comprises:

(a) a therapeutically effective amount of a protein or peptide medicament having a molecular size ranging from about 1K Dalton to about 150 K Daltons which is selected from the group consisting of an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antiinfective, a calcitonin, a hematopoietic factor, a vaccine, a vasoactive peptide, an antisense agent, an oligonucleotide, DNase, a cyclosporin, ribavirin and a mixture of any of the foregoing medicaments;

(b) a non-chlorofluorohydrocarbon fluid propellant carrier for containing said medicament; and (c) a stabilizer selected from an amino acid, a derivative thereof, or a mixture of the foregoing.

2. The formulation as defined in claim 1 wherein said medicament is selected from the group consisting of an insulin analog, an amylin, glucagon, LH-RH, deltirex, leuprolide, gosorelin, nafarelin, octreotide, somatostatin, a calcitonin, porathyroid hormone, TRH, growth hormone-releasing hormone, G-CSF, G-SF, a cytokine, rhDNAse, a heparin, albumin, ovalbumin, aminloride, DDAVP, VIP, a cyclosporin, an erythropoietin, an interferon, IgG, IgE, IgM, IgA, IgD, an interleukin, IRAP, papain, peroxidase, serratio peptidase, catalase, $\alpha$-1-antitrypsin, a gene; a vector, an amiloride, a rhDNAse, an oligonucleotide, ribavirin or a mixture of any of the foregoing medicaments.

3. The formulation as defined in claim 1, wherein said fluid carrier is a hydrocarbon propellant selected from the group consisting of n-butane, propane, isopentane or a mixture thereof.

4. A medicinal aerosol formulation, which consists essentially of:

(a) a therapeutically effective amount of a protein or peptide medicament having a molecular size ranging from about 1K Dalton to about 150 K Daltons which is selected from the group consisting of an insulin, an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antiinfective, a calcitonin, a hematopoietic factor, a vaccine, a vasoactive peptide, an antisense agent, an oligonucleotide, DNase, a cyclosporin, ribavirin and a mixture of any of the foregoing medicaments;

(b) a non-chlorofluorohydrocarbon fluid propellant carrier for containing said medicament; and (c) a stabilizer selected from an amino acid, a derivative thereof, or a mixture of the foregoing.

5. The formulation as defined in claim 4 or claim 1, wherein said stabilizer is selected from the group consisting of the twenty essential and nonessential existing amino acids, any mixture thereof, and any derivative of the foregoing.

6. The formulation as defined in claim 4 or claim 1, wherein said stabilizer is selected from the group consisting of (1) a di-peptide selected from the group consisting of a salt and an ester of oxidized and unoxidized L-cysteinylglycine, gamma-L-glutamyl-L-cysteine, N-acetyl-L-cysteine-glycine; (2) a conjugated, unconjugated or polymeric form of L-Gly-L-Glu and L-Val-L-Thr; (3) L-aspartyl-L-phenylalanine; (4) a muramyl dipeptide; (5) a nutrient selected from the group consisting of L-tyrosyl-L-tyrosine, L-alanyl-L-tyrosine, L-arginyl-L-tyrosine, L-tyrosyl-L-arginine, N-Cbz-L-Leu-L-Leu-OCH and salts or esters of the foregoing; (6) glycyl-glycine; (7) N-acetyl-L-aspartate-L-glutamate; (NAAG); (8) a tripeptide selected from the group consisting of an oxidized and an unoxidized form of gamma-L-glutamyl-L-cysteinylglycine or a muramyl tripeptide and (9) a mixture of any of the foregoing stabilizers.

7. The formulation as defined in claim 4 or claim 1, wherein said fluid carrier is a propellant selected form the group consisting of 1,1,1,2-tetrafluoroethane, 1,1,1,2,3,3,3-heptafluoropropane or a mixture thereof.

8. The formulation as defined in claim 4 or claim 1, which further includes a cosolvent.

9. The formulation as defined in claim 8 wherein said cosolvent comprises ethanol.

10. The formulation as defined in claim 4 or claim 1, which is a dispersion of said medication wherein said stabilizer is present in an amount effective to prevent settling, creaming or flocculation of the formulation for a time sufficient to allow reproducible dosing of the drug after agitation of the formulation.

11. The formulation as defined in claim 10 wherein said stabilizer is present in an amount ranging from about 0.001 parts per million to about 200,000 parts per million of the total weight of the formulation.

12. A method of preparing a stable medicinal aerosol formulation according to claim 4 or claim 1, which comprises:

(a) combining (i) said medicament in an amount sufficient to provide a plurality of therapeutically effective doses, (ii) said fluid carrier in an amount sufficient to propel said plurality of said therapeutically effective doses and (iii) said stabilizer in an amount effective to stabilize the formulation; and (b) dispersing components (i), (ii) and (iii).

13. The method as defined in claim 12 which further comprises combining in step (a) a cosolvent and in step (b) dispersing components (i), (ii) and (iii) with said cosolvent.

14. A method of treating in a human or an animal a condition capable of treatmenty oral or nasal inhalation, which comprises, administering a formulation according to claim 4 or 1 claim to said human or animal by oral or nasal inhalation.

15. A formulation according to claim 4 or claim 1 in an aerosol canister equipped with a metered dose valve.

16. A method of stabilizing a suspension aerosol formulation comprising a non-chlorofluorohydrocarbon propellant and a protein or peptide medicament which is selected from the group consisting of an insulin, an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antiinfective, a calcitonin, a hematopoietic factor, a vaccine, a vasoactive peptide, an antisense agent, an oligonucleotide, DNase, a cyclosporin, ribavirin and a mixture of any of the foregoing medicaments; which comprises incorporating into the formulation a stabilizer selected from the group consisting of a suitable amino acid, a derivative thereof, or any mixture of the foregoing, in an amount which is effective to prevent settling, creaming, or flocculation of the formulation for a time sufficient to allow reproducible dosing of the drug after agitation of the formulation.

17. A metered dose inhaler containing a medicinal aerosol formulation, the formulation which consists essentially of:

(a) a protein or peptide medicament which is selected from the group consisting of an insulin, an insulin analog, an amylin, an immunomodulating protein, an interleukin, an interferon, an erythropoietin, a heparin, a thrombolytic, an antitrypsin, an anti-protease, a hormone, a growth factor, an enzyme, a nucleic acid, an immunoglobulin, an antiinfective, a calcitonin, a hematopoietic factor, a vaccine, a vasoactive peptide, an antisense agent, an oligonucleotide, DNase, a cyclosporin, ribavirin and a mixture of any of the foregoing medicaments in a therapeutically effective amount;

(b) a non-chlorofluorohydrocarbon propellant; and (c) a suitable stabilizer selected from an amino acid, an amino acid derivative, or a mixture of the foregoing, present in an amount sufficient to stabilize the formulation to prevent settling, creaming or flocculation for a time sufficient to allow reproducible dosing of the drug after agitation of the formulation.

18. The metered dose inhaler as defined in claim 17 wherein the stabilizer is selected from the group consisting of the twenty essential and nonessential existing amino acids, any mixture of any of the foregoing and any derivative of the foregoing.

* * * * *